(12) United States Patent
Ding et al.

(10) Patent No.: US 7,682,648 B1
(45) Date of Patent: *Mar. 23, 2010

(54) METHODS FOR FORMING POLYMERIC COATINGS ON STENTS

(75) Inventors: Ni Ding, San Jose, CA (US); Deborra Sanders Millare, San Jose, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1060 days.

This patent is subject to a terminal disclaimer.

(21) Appl. No.: 10/700,710

(22) Filed: Nov. 3, 2003

Related U.S. Application Data

(63) Continuation-in-part of application No. 09/893,957, filed on Jun. 28, 2001, now Pat. No. 6,673,385, which is a continuation-in-part of application No. 09/583,683, filed on May 31, 2000, now abandoned.

(51) Int. Cl.
*A61L 33/00* (2006.01)
*B05D 1/02* (2006.01)
*B05D 3/06* (2006.01)
*C08F 2/46* (2006.01)

(52) U.S. Cl. .............. 427/2.24; 427/2.1; 427/2.25; 427/2.28; 427/421.1; 427/508; 623/1.11; 623/1.44; 623/1.46; 623/1.24; 623/1.2

(58) Field of Classification Search .......... 427/2.1, 427/2.24, 2.25, 2.28; 623/1.1, 1.15, 1.2, 623/1.42, 1.44, 1.46
See application file for complete search history.

(56) References Cited

U.S. PATENT DOCUMENTS

| | | | |
|---|---|---|---|
| 4,329,383 A | 5/1982 | Joh .......................... 428/36 |
| 4,733,665 A | 3/1988 | Palmaz .................... 128/343 |
| 4,800,882 A | 1/1989 | Gianturco ................ 128/343 |
| 4,882,168 A | 11/1989 | Casey et al. ............. 424/468 |
| 4,886,062 A | 12/1989 | Wiktor ..................... 128/343 |
| 4,941,870 A | 7/1990 | Okada et al. .............. 600/36 |
| 4,967,606 A | 11/1990 | Wells et al. ............. 73/864.18 |
| 4,977,901 A | 12/1990 | Ofstead ................... 128/772 |
| 5,015,505 A | 5/1991 | Cetnar |
| 5,112,457 A | 5/1992 | Marchant ................. 204/165 |
| 5,118,779 A | 6/1992 | Szycher ..................... 528/75 |
| 5,165,919 A | 11/1992 | Sasaki et al. ............. 424/488 |
| 5,225,750 A | 7/1993 | Higuchi et al. ........... 318/280 |
| 5,272,012 A | 12/1993 | Opolski .................. 428/423.1 |
| 5,292,516 A | 3/1994 | Viegas et al. ............. 424/423 |
| 5,298,260 A | 3/1994 | Viegas et al. ............. 424/486 |
| 5,300,295 A | 4/1994 | Viegas et al. ............. 424/427 |
| 5,306,501 A | 4/1994 | Viegas et al. ............. 424/423 |
| 5,328,471 A | 7/1994 | Slepian .................... 604/101 |
| 5,330,768 A | 7/1994 | Park et al. ................ 424/501 |
| 5,380,299 A | 1/1995 | Fearnot et al. ............ 604/265 |
| 5,417,981 A | 5/1995 | Endo et al. ............... 424/486 |
| 5,447,724 A | 9/1995 | Helmus et al. ............ 424/426 |
| 5,455,040 A | 10/1995 | Marchant ................. 424/426 |
| 5,462,990 A | 10/1995 | Hubbell et al. ........... 525/54.1 |
| 5,464,650 A | 11/1995 | Berg et al. ................. 427/2.3 |
| 5,527,337 A | 6/1996 | Stack et al. ............... 606/198 |
| 5,569,463 A | 10/1996 | Helmus et al. ............ 424/426 |
| 5,578,073 A | 11/1996 | Haimovich et al. ......... 623/1 |
| 5,605,696 A | 2/1997 | Eury et al. ................ 424/423 |
| 5,609,629 A | 3/1997 | Fearnot et al. ............. 623/1 |
| 5,624,411 A | 4/1997 | Tuch ........................ 604/265 |
| 5,628,730 A | 5/1997 | Shapland et al. ........... 604/21 |
| 5,649,977 A | 7/1997 | Campbell .................... 623/1 |
| 5,658,995 A | 8/1997 | Kohn et al. ................ 525/432 |
| 5,667,767 A | 9/1997 | Greff et al. ............. 424/9.411 |
| 5,670,558 A | 9/1997 | Onishi et al. .............. 523/112 |
| 5,679,400 A | 10/1997 | Tuch ........................ 427/2.14 |
| 5,693,034 A | 12/1997 | Buscemi et al. ............ 604/265 |
| 5,700,286 A | 12/1997 | Tartaglia et al. ............. 623/1 |
| 5,702,754 A | 12/1997 | Zhong ...................... 427/2.12 |
| 5,713,949 A | 2/1998 | Jayaraman .................. 623/1 |
| 5,716,981 A | 2/1998 | Hunter et al. .............. 514/449 |

(Continued)

FOREIGN PATENT DOCUMENTS

EP        0 301 856        2/1989

(Continued)

OTHER PUBLICATIONS

Hanssen et al. "Metallic Wires with an Adherent lubricious and Blood Compatible Polymeric Coating and their Use in the Manufacture of Novel Slippery When Wet Guidewires: Possible Applications Related to Controlled Local Drug Delivery." Journal of Biomedical Materials Research, vol. 48, Issue 6 (pp. 820-828). Nov. 9, 1999.*

(Continued)

*Primary Examiner*—Timothy H Meeks
*Assistant Examiner*—Cachet I Sellman
(74) *Attorney, Agent, or Firm*—Squire, Sanders & Dempsey L.L.P.

(57) ABSTRACT

A method is provided for forming a polymeric coating on a stent. The method can comprise applying a prepolymer or a combination of prepolymers to the stent and initiating polymerization to form a polymeric coating on the stent. The coating material can optionally contain a biologically active agent or combination of agents.

16 Claims, No Drawings

U.S. PATENT DOCUMENTS

| | | | |
|---|---|---|---|
| 5,735,897 A | 4/1998 | Buirge | 623/12 |
| 5,746,998 A | 5/1998 | Torchilin et al. | 424/9.4 |
| 5,766,710 A | 6/1998 | Turnlund et al. | 428/36.1 |
| 5,769,883 A | 6/1998 | Buscemi et al. | 623/1 |
| 5,776,184 A | 7/1998 | Tuch | 623/1 |
| 5,782,908 A * | 7/1998 | Cahalan et al. | 623/1.13 |
| 5,788,979 A | 8/1998 | Alt et al. | 424/426 |
| 5,800,392 A | 9/1998 | Racchini | 604/96 |
| 5,804,318 A * | 9/1998 | Pinchuk et al. | 428/421 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,824,056 A | 10/1998 | Rosenberg | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,843,172 A | 12/1998 | Yan | 623/1 |
| 5,851,508 A | 12/1998 | Greff et al. | 424/9.411 |
| 5,858,746 A | 1/1999 | Hubbell et al. | 435/177 |
| 5,863,650 A * | 1/1999 | Healy et al. | 428/336 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,402 A | 7/1999 | Nacker et al. | 427/7 |
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,005,020 A | 12/1999 | Loomis | 523/105 |
| 6,010,530 A | 1/2000 | Goicoechea | 623/1 |
| 6,013,855 A * | 1/2000 | McPherson et al. | 623/23.76 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,083,524 A | 7/2000 | Sawhney et al. | 424/426 |
| 6,096,070 A | 8/2000 | Ragheb et al. | 623/1 |
| 6,099,562 A | 8/2000 | Ding et al. | 623/1.46 |
| 6,100,346 A * | 8/2000 | Jamiolkowski et al. | 525/419 |
| 6,107,416 A * | 8/2000 | Patnaik et al. | 525/453 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 606/108 |
| 6,221,425 B1 | 4/2001 | Michal et al. | 427/2.25 |
| 6,231,600 B1 | 5/2001 | Zhong | 623/1.42 |
| 6,240,616 B1 | 6/2001 | Yan | 29/527.2 |
| 6,242,041 B1 | 6/2001 | Katoot et al. | 427/2.24 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,290,729 B1 * | 9/2001 | Slepian et al. | 623/23.72 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,368,658 B1 * | 4/2002 | Schwarz et al. | 427/2.15 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 * | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,632,446 B1 | 10/2003 | Hubbell et al. | |
| 6,673,385 B1 * | 1/2004 | Ding et al. | 427/2.28 |
| 2001/0014717 A1 * | 8/2001 | Hossainy et al. | 525/60 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.24 |
| 2003/0065377 A1 | 4/2003 | Davila et al. | 623/1.13 |
| 2003/0099712 A1 | 5/2003 | Jayaraman | 424/486 |
| 2003/0108588 A1 | 6/2003 | Chen et al. | |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/23222 | 6/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |

| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 947-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inou et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct., 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

METHODS FOR FORMING POLYMERIC COATINGS ON STENTS

CROSS-REFERENCES

This application is a continuation-in-part of U.S. patent application Ser. No. 09/893,957 filed on Jun. 28, 2001, issued as U.S. Pat. No. 6,673,385 on Jan. 6, 2004, which is a continuation-in-part of U.S. patent application Ser. No. 09/583,683 filed on May 31, 2000 now abandoned.

BACKGROUND

1. Field of the Invention

This invention relates to a method for coating stents.

2. Description of the Background

Stents act as scaffoldings, functioning to physically hold open and, if desired, to expand the wall of a passageway. Typically stents are capable of being compressed, so that they can be inserted through small vessels via catheters, and then expanded to a larger diameter once they are at the desired location. Mechanical intervention via stents has reduced the rate of restenosis; restenosis, however, is still a significant clinical problem. Accordingly, stents have been modified not only to perform as a mechanical scaffolding, but also to provide biological therapy.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A common method of medicating a stent is by depositing a polymeric coating, impregnated with the therapeutic substance, on the surface of the stent. A polymer dissolved in a solvent is applied to the stent. A therapeutic substance can be dissolved or dispersed in the composition. The solvent is allowed to evaporate to form the coating. The application of the composition can be performed by spraying the composition on the stent or immersing the stent in the composition. A problem associated with the application of a polymeric solution includes coating defect such as "cob webs" and "pool webs." "Cob webs" are defined as the gathering of the polymeric coating between the stent struts once the solvent has been removed. "Pool webs" are clumps or pools of polymer on the struts. "Cob webs" and "pool webs" are caused by high viscosities associated with the composition and the surface tension of the polymer and the solvent. Moreover, increasing the quantity of the polymer applied to the stent, so as to increase the drug loading of the stent, further promulgates the development of such defects. Accordingly, a method is needed to reduce or significantly eliminate coating defects on a stent.

SUMMARY

A method of forming a polymeric coating on a stent is provided, the method comprises applying a monomer or a combination of monomers to the stent, and polymerizing the monomer or combination of monomers to form a polymeric coating for the stent, wherein the polymeric coating comprises a thermoplastic linear polymer. Applying of the monomer(s) can be conducted by spraying the monomer(s) at the stent. The polymerization can be carried out by radical chain reaction or step-function reaction. The polymerization can be initiated by the inclusion of an initiator, such as a thermal initiator, a photo initiator, a redox initiator, an initiator for radiation initiation, or an initiator for electroinitiation. In an embodiment where a photo initiator is used, the initiator can be mixed with monomer(s) followed by the exposure of the stent to a light energy source. In an embodiment where a thermal initiator is used, the initiator can be mixed with monomer(s) followed by the exposure of the stent to a thermal energy source. In one embodiment the monomer(s) can be in a liquid phase or can be added to a solvent or a combination of solvents to effect dissolution of the monomer(s). The method can also include applying an active agent to the stent. The active agent can be applied separately or added to the monomer or at least one of the monomers of the combination.

A method of forming a polymeric coating on a stent is provided, the method comprises spraying a radially expandable stent with a coating fluid, the fluid comprising a prepolymer and an therapeutic agent mixed with the prepolymer, and causing the prepolymer to react to form a polymeric coating on the stent, wherein the active agent is contained in the polymeric coating, and wherein the polymer forming the coating is a thermoplastic linear polymer. The coating fluid can optionally include an additive for increasing the viscosity of the fluid.

A method of forming a polymeric coating for a stent is provided, the method comprises applying an oligomer or a combination of oligomers to the stent, and polymerizing the oligomer or combination of oligomers to form a polymeric coating for the stent, wherein the polymeric coating comprises a thermoplastic linear polymer.

A method of forming a polymeric coating for a stent is provided, the method comprises applying a macromer or a combination of macromers to the stent, and polymerizing the macromer or combination of macromers to form a polymeric coating for the stent, wherein the polymeric coating comprises a thermoplastic linear polymer free from units derived from a dicarboxylic acid.

DETAILED DESCRIPTION

1. Terms and Definitions

All the terms in the present application pertaining to general chemistry, organic chemistry, and polymer science, including polymer chemistry and polymer physics, have meanings corresponding to definitions used by the International Union of Pure and Applied Chemistry (IUPAC). The following terminologies and definitions apply:

The term "monomer" is defined as the building material from which a polymer is formed such as by step-function (condensation), radical chain (addition), or ionic polymerization processes. The monomer can be any chemical which can be polymerized to form a suitable, biocompatible coating on the stent. The term "monomer" is further defined as a synonym of the term "monomeric chemical compound." Monomeric chemical compounds are to be distinguished from oligomers and macromonomers.

The term "oligomer" is defined as a polymer intermediate containing relatively few structural units.

The term "macromer" is defined as a polymer macromolecule of which has at the minimum a reactive group at one end or inside the chain. Such macromolecule can undergo further polymerization via the reactive group thereby contributing constitutional units to the essential structure of the polymer. The term "macromer" is further defined as a synonym of the term "macromonomer."

The term "polymer" is defined to be inclusive of homopolymers and copolymers (further defined below), including any of the following:
   (a) random copolymers;
   (b) alternating copolymers;
   (c) cross-linked polymers;
   (d) linear polymers (including strictly organic polymers);
   (e) thermoplastic polymers;
   (f) branched polymers (including brush polymers);
   (g) block-copolymers; and
   (h) graft polymers.

The term "polymer" is further defined as a synonym of the term "polymeric compound." The term "copolymer" is defined as a polymer derived from more than one species of monomer, including copolymers that are obtained by copolymerization of two monomer species, those obtained from three monomers species ("terpolymers"), those obtained from four monomers species ("quaterpolymers"), etc.

The term "random copolymer" is defined as a copolymer consisting of macromolecules in which the probability of finding a given monomeric unit at any given site in the chain is independent of the nature of the adjacent units. In a random copolymer, the sequence distribution of monomeric units follows Bernoullian statistics.

The term "alternating copolymer" is defined as a copolymer consisting of macromolecules comprising two species of monomeric units in alternating sequence.

The term "cross-linked polymer" is defined as a polymer which includes at least one cross-link. "Cross-link" is defined as a region in a macromolecule from which at least four chains emanate, and which is formed by reactions involving sites or groups on existing macromolecules or by interactions between existing macromolecules. The region defining the "cross-link" can be an atom, a group of atoms, or a number of branch points connected by bonds, groups of atoms, or oligomeric chains.

The term "linear polymer" is defined as a macromolecule the structure of which essentially comprises a multiple repetition, in linear sequence, of units derived from low relative molecular mass molecules. The term "strictly organic polymer" is defined as a polymer that is comprised only of atoms of carbon, hydrogen, oxygen, nitrogen and/or halogens such as chlorine, fluorine, bromine and iodine. Whenever the term "strictly organic polymer" is used, it is provided that the polymers containing hetero atoms are specifically excluded. "Hetero atoms" are atoms other than carbon, hydrogen, oxygen, nitrogen and/or halogens. Representative examples of hetero atoms include, but are not limited to, silicon, sulfur, phosphorous, selenium, tellurium, and antimony.

The term "thermoplastic polymer" is defined as a polymer that is not capable of forming cross-links, and consequently does not form any cross-links even when it is heated, whether in the presence of a catalyst of cross-linking or in the absence of such catalyst. Typically, the cross-links are not formed because the thermoplastic polymers lacks reactive chemical fragments in their macromolecules needed for forming the cross-link. Examples of such reactive chemical fragments include π-bonds (as in double and triple bonds) and reactive functional groups, such as hydroxyl, carboxyl, amino, epoxy, urethane, etc. As a result, a thermoplastic polymer can be softened and fused when heated and become rigid again when cooled. A cycle of re-melting and re-solidifying of a thermoplastic polymer can be repeated unlimited number of times, without the polymer undergoing any appreciable chemical change. Also, a thermoplastic polymer soluble in a solvent remains soluble in that solvent after being subjected to any number of melting/solidifying cycles.

The polymers that are both linear and thermoplastic are defined as "linear thermoplastic polymers." For the purposes of the present application, whenever the terms "linear polymer," or "thermoplastic polymer," or "linear thermoplastic polymer" are used, these terms are intended to specifically exclude any polymers, macromolecules of which have any cross-links. In other words, as used in the present application, "linear polymers" and/or "thermoplastic polymers" are completely free of any cross-linked fragments.

The term "branched polymer" is defined as a polymer having a chain with at least one branch point between the boundary units. A "branched point" is defined as a point on a chain at which a branch is attached. A "branch" is defined as an oligomeric or polymeric, but not a monomeric, offshoot from the macromolecular backbone chain. In other words, if an offshoot from the macromolecular backbone chain is a short monomeric structure, such as a hydrogen atom, a small alkyl group (e.g., $C_1$-$C_8$ alkyl group), or a pendant substitutent (e.g., —OH, —COOH, —$NH_2$, and the like), the polymer is "linear," and is not defined as "branched." "Brush polymer" is a variation of the "branched polymer" having at least some branch points with functionality greater than three.

The term "block copolymer" is defined as a copolymer containing a linear arrangement of blocks, a block being defined as a portion of a polymer molecule in which the monomeric units have at least one constitutional or configurational feature absent from the adjacent portions. For example, a block copolymer of moiety A and moiety B may be written as -A-A-A-B-B-B-B-. Such block copolymer is often referred to as a "AB block copolymer." The blocks need not be linked on the ends, since the individual blocks are usually long enough to be considered polymers in their own right. The AB block copolymer can be, accordingly, named poly A-block-poly B. The term "block copolymer" is intended to broadly include copolymers having two or more types of blocks, for example, di-block copolymer and tri-block copolymers.

The term "graft polymer" is defined as a polymer having a macromolecule with one or more species of blocks connected to the main chain as side-chains, the side-chains having constitutional or configurational features that differ from those in the main chain.

The term "prepolymer" is defined to be inclusive of one or a combination of different monomers, oligomers, and macromers that are capable of forming a polymer. Thus, a "prepolymer" is a precursor of a polymer. Should any of the prepolymers be in a solid phase at operating temperatures, e.g., ambient temperature and pressure, the prepolymer can be dissolved in a solvent system for application to a stent.

The term "multi-carboxylic acid" is defined as an organic acid having more than one carboxylic (organic acid) group —COOH. One species of "multi-carboxylic" acid is a dicarboxylic acid having two —COOH groups.

2. Embodiments of the Invention

In accordance with one embodiment, a monomer or a combination of monomers can be applied to a stent for coating the stent to serve as prepolymer(s). Examples of the monomer can include, but are not limited to, vinyl acrylate and allyl compounds such as any monomer with one or more vinyl, acrylate and/or allyl double bonds. Specific examples of some monomers that can be used include acrylic acid, methacrylic acid, 2-hydroxyethyl methacrylate (HEMA), glycol methacrylate, methyl methacrylate, ethyl methacrylate, n-butyl methacrylate, sulfanato ethyl methacrylate, ethylene, vinyl acetate, ethyl acrylate, acrylamide, divinyl benzene, triethylene glycol divinyl ether; tri-methylol propane triacrylate; pentaerythritol tetraacrylate, Bisphenol A ethoxylate diacrylate, allyl ether, diallyl maleate, vinylidene fluoride, hexafluoropropene, and triallyl isocyanurate.

Additionally, unsaturated monomers such as cell adhesion promoting, non-fouling, or anti-restenotic monomers can be also used as prepolymers to form the coating or as additives to be used in conjunction with other prepolymers. Examples include vitamin E methacrylate, phenoxyethylmethacrylate, dimethyl amino ethyl methacrylate, vinyl pyrrolidone, polyethylene glycol methacrylate, sulfonated Dextran, methacryloxy phosphoryl choline, methacrylate acid, acryloyl, and methacryloyl. The combination of different monomers can form polymers with properties suitable for drug impregnation and stent coating.

Subsequent to the application of any of the compounds described above and serving as a prepolymer(s), or of any combination thereof, polymerization of the prepolymer(s) is induced. As a result, a polymeric coating is formed on the stent. In one embodiment, the polymeric coating that is formed can comprise a linear polymer. The linear polymer that is formed on the stent can be a strictly organic polymer.

In one embodiment, the linear polymer forming the stent coating can include exclusively a non-cross-linked linear thermoplastic polymer. In another embodiment, the bulk of the stent coating can be comprised of a non-cross-linked linear thermoplastic polymer, with the balance of the coating comprising a small amount of a cross-linked polymer, for example, between greater than 0 mass % and less than about 5 mass % of the cross-linked polymer. In yet another embodiment, the non-cross-linked linear thermoplastic polymers can be free of units derived from a multi-carboxylic acid, such as a dicarboxylic acid.

Examples of the linear polymers of which the polymeric stent coatings can be comprised include poly(acrylic acid), poly(methacrylic acid), poly(2-hydroxyethyl methacrylate), poly(glycol methacrylate), poly(methyl methacrylate) (PMMA), poly(ethyl methacrylate)(PEMA), poly(n-butyl methacrylate)(PBMA), poly(sulfanato ethyl methacrylate), poly(ethylene-co-vinyl acetate)(PEVA), poly(ethyl acrylate) (PEA), poly(acrylamide)(PAA), poly(divinyl benzene), poly(triethylene glycol divinyl ether), poly(allyl ether), poly(diallyl maleate), poly(vinylidene fluoride)(PVDF), and poly(vinylidene fluoride-co-hexafluoropropene)(PVDF-HFP). Those having ordinary skill in the art will recognize that many of these polymers are linear thermoplastic polymers, e.g., PMMA, PEMA, PBMA, PEA, PAA, PVDF, and PVDF-HFP.

To carry out polymerization of a prepolymer described above, the process of polymerization can include initiation. For example, photoinitiation as is well understood by those having ordinary skill in the art can be used. Briefly, light of short enough wavelength (e.g., 320-800 nm) or, in other words, high enough energy per quantum can initiate polymerization directly. The light energy can be provided by any appropriate source to generate the desired radiation, such as mercury-arc lamps, fluorescent lamps with special phosphors, long wave ultra violet lamps, helium-neon laser or an argon ion laser. Photochemical initiators can be used to generate free radicals which propagate polymerization. Some examples of photochemical initiator that can be used include benzophenone, 2,2-dimethoxy-2-phenylacetophenone, 1-hydroxycyclohexyl phenyl ketone, benzoin ethyl ether, and phenyl azide. With the use of photoinitiation, the rate of generation of free radicals can be controlled with high precision by controlling the intensity of the initiating light.

Other kinds of initiators can also be used, such as, for example, thermal initiators. To provide for thermal initiation, thermal initiators forming free radicals at moderate temperatures can be used. Free radical polymerization initiators are compounds with bonds that easily undergo thermal hemolytic scission, e.g., hydroperoxides (RO—OH); peroxides (RO—OR'), peresters (RCOO—OR'), azo compounds (RN═NR') and persulfate compounds ($O_4S$—$SO_4$). These initiators thermally decompose at the illustrated bond. Representative examples can include benzoyl peroxide, with or without triethanolamine, potassium persulfate, with or without tetramethylethylenediamine, bis(2,4-dichlorobenzoyl) peroxide; dicumyl peroxide; 2,5-bis(tert-butyl peroxy)-2,5-dimethyl hexane; ammonium persulfate, and 2,2'-azobisisobutyronitrile and ammonium persulfate with sodium bisulfite. Each initiator requires a different temperature to induce decomposition.

Another type of initiation that can be used is initiation by high-energy radiation from a wide variety of sources, including electrons, gamma rays, x-rays, and slow neutrons. These are effective in producing free radicals that can initiate polymerization of monomers. Another type of initiation that can be used is initiation via redox initiators. Yet other types of initiation that can be used are initiation by UV radiation and electroinitiation.

In accordance with another embodiment, an oligomer or combination of oligomers can be used to coat the stent. A representative example includes urethane-acrylate (e.g., Cognis 6892, formerly Henckel 12-892). Subsequent to the application of oligomer(s), polymerization of the oligomer(s) is induced. As a result, a polymeric coating is formed on the stent. In one embodiment, the polymeric coating that is formed can comprise a linear polymer. The linear polymer derived from oligomer(s) that is formed on the stent can be a strictly organic polymer. In one embodiment, the linear polymer derived from oligomer(s) can include exclusively a non-cross-linked linear thermoplastic polymer.

In accordance with another embodiment, a macromer or a combination of macromers can be used to coat the stent. Representative examples include, but are not limited to, polyethylene glycol (PEG) diacrylate, polycaprolactone diacrylate, polysaccharide-PEG acrylate, e.g. heparin-PEG acrylate and hyaluronate-PEG acrylate. Subsequent to the application of any of the macromer(s) described above, or of any combination thereof, polymerization of the macromer(s) is induced. As a result, a polymeric coating is formed on the stent. In one embodiment, the polymeric coating that is formed can comprise a linear polymer. The linear polymer derived from macromer(s) that is formed on the stent can be a strictly organic polymer. In one embodiment, the linear polymer derived from macromer(s) can include exclusively a non-cross-linked linear thermoplastic polymer.

In accordance with another embodiment of the present invention, an active agent can be combined with the prepolymer or with a solvent system in which such the prepolymer is dissolved. Alternatively, the active agent can be co-applied or pre-applied by any suitable liquid carrier. The active agent should be applied as a true solution or a saturated solution. If the active agent is not completely soluble, operations including mixing, stirring, and/or agitation can be employed to effect homogeneity of the residues. The active agent may be added in fine particles. The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent or a drug can also include any substance capable of exerting a therapeutic or prophylactic effect in the practice of the present invention. The drug may include small molecule drugs, peptides or proteins.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. TAXOTERE®, from Aventis S.A., Frankfurt, Germany) methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (bivalirudin, Biogen, Inc., Cambridge, Mass.). Examples of such cytostatic or antiproliferative agents include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the name of everolimus, available from Novartis), 40-O-(3-hydroxy)propyl-rapamycin, 40-O-[2-(2-hydroxy)ethoxy]ethyl-rapamycin, and 40-O-tetrazole-rapamycin.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Representative examples of solvent systems for effectuating the dissolution, should the prepolymer be in solid phase, include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methylpyrrolidinone, toluene and mixtures thereof.

In accordance with another embodiment, a fluid can be used to adjust or increase the "wetting" of the prepolymer or the solvent system or to increase the solubility of the active agent in the prepolymer or the solvent system. Accordingly, higher active agent concentrations can be formulated. "Wetting" is defined by capillary permeation. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of the wetting fluid include, but are not limited to, tetrahydrofuran (THF), dimethylformamide (DMF), 1-butanol, n-butyl acetate, dimethylacetamide (DMAC), and mixtures and combinations thereof.

To form a coating on the stent, the prepolymer or combination of prepolymers with or without a solvent system can be applied to both the inner and outer (the tissue contacting) surface of the stent. Application can be by any method, for example, by spraying the composition onto the stent, by immersing the stent in the composition, by chalking (automated or hand-applied), or by micro-deposition of the coating solution to the surface of a textured stent. If more than one monomer, oligomer or macromer is employed, each prepolymer can be combined and applied as a single solution the stent concomitantly in the spray application, or each compound can be applied in a sequence of application steps. Because prepolymers, specially monomers, have a relatively low viscosity, some of which can be less than 2.5 centipoise at room temperature, the use of prepolymers for making a polymeric coating would allow for a more fluent application of the coating which can minimize coating defects such as "cob webs" or "pool webs." Should the viscosity of the monomer be too low so as not to allow a suitable retention of the monomer on a stent, a viscosifying agent may be required. Examples of the viscosifying agents can include polymers of the same prepolymer(s) such as polyvinyl pyrrolidone and poly-n-butylmethacrylate. Other examples can include glucose, caster oil, cotton seed oil, and glycerol. The molar ratio of the viscosifying agent could be less than 60%, more narrowly less than 50% of the prepolymer. An alternative method of increasing the retention of the prepolymer on the surface of the device would be to decrease the temperature during and/or subsequent to the application of the prepolymer to below room temperature. Providing a cooler environment leads to an increase in the viscosity.

In addition to creating a less viscose delivery platform, monomeric compounds may allow for a better dissolution of the active agent with the monomer or the monomer-solvent combination. Many of the active agents are hydrophilic and can only dissolve with highly polar counterparts. Polymers have a tendency of being less polar than their monomeric constituents. Accordingly, a better dissolution is achieved by the use of a monomeric delivery system.

The prepolymers can be used to form a basecoat or a primer layer, a reservoir layer, and/or a topcoat or rate limiting barrier layer. As for deposition of the outermost coating layer, a second functional or anchoring monomer can be included in the formulation which would allow for the surface modification of the outermost layer. For example, the addition of a small amount of allyl amine or N-(3-aminopropyl)-methacrylamide, acrylic or methacrylic acid, isocyanato ethyl methacrylate, or cinnamaldehyde could introduce, respectively, amino, carboxyl, isocyanate, or aldehyde functional groups on the surface of the layer. Accordingly, biocompatible components such as heparin and polyethylene glycol can be covalently bonded to the surface of the coating.

The type of stent used in the practice of the present invention is not of critical importance. Stents are broadly defined to include radially expandable stents such as balloon-expandable stents or self-expandable stents and stent-grafts. The stents can be vascular or non-vascular type stents. One of ordinary skill in the art understands that the coating application of the present invention can also be used with a variety of other medical devices, such as grafts, heart valves, endocardial leads, and other implantable devices. The stent can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the process.

3. EXAMPLES

Embodiments of the present invention can be further illustrated by the following examples.

Example 1

A monomer n-butyl methacrylate (BMA) can be mixed with an initiator azo-bis(isobutyronitrile) (AIBN) to form a BMA/AIBN mixture having the mass ratio between AIBN and BMA of about 1:100. The mixture can be sprayed on the surface of a stent. The stent can be baked at a temperature of at least about 50° C. to initiate radical polymerization. As a result of polymerization, poly(n-butyl methacrylate)(PBMA) coating can be obtained, to form a coating on the surface of the stent. To increase the weight or thickness of the coating, small amounts of PBMA (e.g., less than about 1 mass %) can be added to the initial mixture to increase the viscosity, or the coating and baking cycle can be repeated until a desired weight or thickness is reached.

Example 2

A composition containing about 25 mole % methylmethacrylate (MMA), about 0.9 mole % BMA, about 8 mole % PEG methacrylate having molecular weight of about 6,000 Daltons, about 3 mole % photo-initiator, and the balance, dimethylacetamide solvent (DMAC) can be prepared. The composition can be sprayed on the stent. UV illumination can be applied for about 10 minutes. A non-solvent such as hexane can be added to precipitate the final polymer.

Example 3

A composition containing about 9 mole % BMA, about 8 mole % PEG methacrylate having molecular weight of about 6,000 Daltons, about 20 mole % sulfanato ethyl methacrylate, about 20 mole % ethanol, about 3 mole % photo-initiator, and the balance, DMAC solvent can be prepared. The composition can be sprayed on the stent. UV illumination can be applied for about 10 minutes. A non-solvent such as hexane can be added to precipitate the final polymer.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of forming a polymeric coating on a stent, comprising:
    (a) spraying a radially expandable stent with a coating fluid, the coating fluid comprising a prepolymer, a bioactive agent mixed with the prepolymer, and an additive for increasing the viscosity of the fluid; and
    (b) causing the prepolymer to react to form a polymeric coating on the stent;
    wherein the prepolymer comprises a hydrophobic macromer comprising structural units of a polymer, wherein the bioactive agent is contained in the polymeric coating, and wherein the polymer forming the coating is a thermoplastic linear polymer comprising a multiple repetition of units derived from the macromer or combination of macromers in linear sequence and is free from cross-linked fragments.

2. The method of claim 1, wherein the coating fluid further comprises a solvent or a combination of solvents.

3. The method of claim 1, wherein the prepolymer is in a fluid phase at room temperature.

4. The method of claim 1, wherein the prepolymer comprises acrylate, vinyl or allyl compounds.

5. The method of claim 1, wherein the bioactive agent is for the treatment of restenosis.

6. The method of claim 1, wherein the act of causing the prepolymer to react comprises initiation by step-function reaction, radical chain reaction, or ionic polymerization processes.

7. The method of claim 1, additionally comprising applying to the stent a second fluid comprising at least one other prepolymer, different than the prepolymer of the coating fluid, wherein the prepolymers of the coating fluid and second fluid are capable of reacting to form a polymeric coating.

8. The method of claim 1, additionally comprising applying to the stent a monomer for creating functional groups on the surface of the polymeric coating.

9. The method of claim 1, further comprising combining an initiator of polymerization with the prepolymer.

10. The method of claim 9, wherein the initiator is selected from the group consisting of a thermal initiator, a photo initiator, a redox initiator, an initiator for radiation initiation and an initiator for electroinitiation.

11. The method of claim 1, wherein the additive is selected from the group consisting of glucose, caster oil, cotton seed oil, glycerol, poly(vinyl pyrrolidone), and poly(n-butylmethacrylate), and any combination thereof.

12. A method of forming a polymeric coating for a stent, comprising:
   (a) applying polycaprolactone diacrylate to the stent; and
   (b) polymerizing the polycaprolactone diacrylate to form a polymeric coating for the stent;
   wherein the polymeric coating comprises a thermoplastic linear polymer comprising a multiple repetition of units derived from the polycaprolactone diacrylate in linear sequence and is free from cross-linked fragments.

13. A method of forming a polymeric coating on a stent, comprising:
   (a) spraying a radially expandable stent with a coating fluid, the coating fluid comprising a prepolymer and a bioactive agent mixed with the prepolymer;
   (b) causing the prepolymer to react to form a polymer; and
   (c) adding a non-solvent to precipitate the polymer formed by the reaction of the prepolymer such that a polymeric coating is formed on the stent;
   wherein the prepolymer comprises a hydrophobic macromer comprising structural units of the polymer, wherein the bioactive agent is contained in the polymeric coating, and wherein the polymer forming the coating is a thermoplastic linear polymer comprising a multiple repetition of units derived from the macromer or combination of macromers in linear sequence and is free from cross-linked fragments.

14. A method of forming a polymeric coating on a stent, comprising:
   (a) spraying a radially expandable stent with a coating fluid, the coating fluid comprising a prepolymer, a bioactive agent mixed with the prepolymer, and a wetting fluid; and
   (b) causing the prepolymer to react to form a polymeric coating on the stent;
   wherein the prepolymer comprises a hydrophobic macromer comprising structural units of a polymer, wherein the bioactive agent is contained in the polymeric coating, and wherein the polymer forming the coating is a thermoplastic linear polymer comprising a multiple repetition of units derived from the macromer or combination of macromers in linear sequence and is free from cross-linked fragments.

15. The method of claim 14, wherein the wetting fluid is selected from the group consisting of tetrahydrofuran, dimethylformamide, 1-butanol, n-butyl acetate, dimethylacetamide (DMAC), and any combination thereof.

16. A method of forming a polymeric coating for a stent, comprising:
   (a) applying n-butyl methacrylate and an initiator to the stent; and
   (b) polymerizing the n-butyl methacrylate to form a poly(n-butylmethacrylate) polymeric coating for the stent;
   wherein the polymeric coating comprises a thermoplastic linear polymer.

* * * * *